United States Patent [19]

Prud'Homme et al.

[11] Patent Number: 5,130,171
[45] Date of Patent: Jul. 14, 1992

[54] PROCESS FOR ENCAPSULATING PARTICLES WITH A SILICONE

[75] Inventors: Christian Prud'Homme, Lyons; Hugues Porte, Caluire, both of France

[73] Assignee: Rhone-Poulenc Sante, Antony, France

[21] Appl. No.: 454,426

[22] Filed: Dec. 21, 1989

[30] Foreign Application Priority Data

Dec. 22, 1988 [FR] France .................. 88 17274

[51] Int. Cl.⁵ .................. B01J 13/04; B05D 7/24
[52] U.S. Cl. .................. 427/213.36; 47/57.6; 424/462; 424/497; 424/501; 427/212; 427/213
[58] Field of Search .................. 427/213.36, 212, 213; 424/462, 497, 501; 514/963

[56] References Cited

U.S. PATENT DOCUMENTS

| | | | |
|---|---|---|---|
| 3,141,792 | 7/1964 | Lachman et al. | 427/3 X |
| 3,247,066 | 4/1966 | Milosovich, Jr. | 424/495 |
| 3,832,252 | 8/1974 | Higuchi et al. | 424/486 X |
| 3,911,183 | 10/1975 | Hinkes | 427/213 X |
| 3,921,636 | 11/1975 | Zaffaroni | 424/468 X |
| 3,943,063 | 3/1976 | Morishita et al. | 427/213.36 |
| 4,230,686 | 10/1980 | Schofflin et al. | 424/486 X |
| 4,851,216 | 7/1989 | Lee | 424/486 X |

*Primary Examiner*—Richard D. Lovering
*Attorney, Agent, or Firm*—Morgan & Finnegan

[57] ABSTRACT

Particles of active substance are encapsulated by spraying them with a thermoplastic silicone copolymer in solution in an organic solvent or in an aqueous dispersion or emulsion and removing the solvent or water by drying with hot air. The spraying/drying process employed is, for example, the Wurster process. The copolymer employed can be made up of a succession of polydiorganosiloxane segments or blocks and of organic segments or blocks (polyesters, polyethers, polyurethanes, polystyrenes, and the like). It can also be a polydiorganosiloxane grafted with organic chains. The active substance is in the form of particles with a particle size of between 50 μm and 5 mm. It may be a catalyst, a perfume, a colorant, a cosmetic product, a medication, a plant-protection product, plant seeds, and the like.

The invention is especially useful for controlling the release of active substance in an aqueous medium.

7 Claims, No Drawings

PROCESS FOR ENCAPSULATING PARTICLES WITH A SILICONE

FIELD OF THE INVENTION

The encapsulation of active substances in the form of particles having a particle size from a few μm to a few millimeters has acquired considerable importance, chiefly (but not only) in the pharmaceutical and plant-protection field.

BACKGROUND OF THE INVENTION

This encapsulation is intended to protect the active substance and then to allow its release in a controlled manner, especially into an aqueous medium.

Silicone polymers have been employed for a long time in encapsulating coatings for active substances, and silicone polymers have two properties that are of value in applications of this type, namely their biocompatibility and their permeability to gases and to small molecules.

Silicones are generally employed in the form of macromolecules bearing reactive chemical functional groups which are crosslinked at the surface of the active substance to form a coating which is made up of crosslinked polymers that are insoluble in common organic solvents. This state of the art is illustrated by patents EP-A-267,003, EP-A-280,400 and U.S. Pat. No. 4,370,160.

According to this art, the crosslinking of these silicone polymers takes place in the presence of the active substance. This crosslinking is generally carried out using an organometallic curing catalyst, by heating or by irradiation (with ultraviolet, infrared, electron beam, gamma) or a combination of these means. Since this crosslinking involves chemical or photochemical reactions in the presence of the active substance, it can therefore have a detrimental effect on this active substance.

Furthermore, the intrinsic physicochemical properties of the active substance may interfere with or even completely inhibit the crosslinking process, and this problem is particularly severe when the active substance contains a thiol functional group.

In addition, the biocompatible nature of the polymer is of crucial importance in pharmaceutical and biological applications. It is difficult to remove from the polymer used to encapsulate an active substance undesirable products such as catalysts and residual polymers which are not integrated into the crosslinked material.

At the present time, the process of encapsulation by successive film-coating, which is the most effective from the technical standpoint for producing the encapsulation of active substances, comprises at least one stage of spraying a film-forming composition containing an organic polymer in solution in an organic solvent or in the form of an aqueous emulsion or dispersion followed by at least one drying operation, that is to say evaporation of the organic solvent and/or water.

An example of a process of this kind is the process known by the name of "spray coating", according to which the particles to be encapsulated are stirred (fluidized) by a gas stream which also ensures their drying, that is to say the evaporation of the organic solvent and/or water.

The film-forming composition is sprayed by one or more nozzles situated in various regions of the reactor depending on the process type employed, for example, above, within or at the base of the cloud of particles.

Thus, this spraying is at the base of the fluidized bed of particles in the Wurster process. The Wurster spraying technique is described in detail in patents U.S. Pat. Nos. 2,799,241, 3,089,824, 3,117,027, 3,196,827, 3,207,824, 3,241,520, 3,253,994 and EP-A-188,953.

In order to use the valuable physico-chemical properties of silicones in the spraying/drying process without having the disadvantages of crosslinked materials, a person skilled in the art may be inclined to think of employing oily or resinous diorganopolysiloxane polymers which are not crosslinkable, that is to say unreactive in a film-coating process using spraying/drying of particles of active substances.

Unfortunately, as is demonstrated in the comparative examples of the present application, these unreactive silicone oils or resins are particularly unsuited for implementing the process of encapsulation using spraying/drying.

In fact, during the encapsulation process, and consequently even more at the end of the process, the encapsulated particle has a marked tendency to agglomeration due to the adhesive and sticky nature of the silicone polymer. Moreover, even in the absence of the adhesive nature, the silicone coating tends to creep and the particle is no longer perfectly encapsulated.

In the process of the present invention a class of polymer is employed for encapsulating particles of active substance which has the same advantages as the known silicone polymers, but without disadvantages of capsules of crosslinked silicone polymers and the disadvantages of capsules of unreactive silicone polymers.

DESCRIPTION OF THE INVENTION

According to the present invention, particles of active substance with a mean particle size of between 50 μm and 5 mm are encapsulated, by film-coating each particle with a thermoplastic silicone copolymer, by spraying onto each particle the said polymer in solution in an organic solvent or in aqueous emulsion or dispersion, and evaporating the solvent and/or the water.

The thermoplastic silicone copolymers which can be employed in the present invention are chosen from linear multiblock copolymers, block copolymers and graft copolymers, whose substantially linear main polymer chain consists either of an alternation of polydiorganosiloxane segments or blocks and of organic segments or blocks, or of a polydiorganosiloxane chain onto which organic chains are grafted.

The organic radicals of the diorganosiloxyl units are preferably $C_1$–$C_4$ alkyl radicals, in particular, methyl, 3,3,3-trifluoropropyl radicals and phenyl radicals.

The thermoplastic copolymers which can be employed in the present invention are polymers which soften under the effect of heat, which are soluble in certain organic solvents and/or are emulsifiable or dispersible in water by the usual methods, and whose use involves reversible physical processes.

The preferred thermoplastic copolymers are those which have a Tg (glass transition temperature) or melting temperature (in the case of semicrystalline copolymers) which is above the ambient temperature (25° C.) and preferably above 40° C. and generally below 200° C.

The thermoplastic silicone copolymers are preferably are soluble in volatile organic solvents whose evaporation rates are preferably high. These solvents, employed by themselves or mixed, may be, for example, chloroform, acetone, methyl ethyl ketone, tetrahydrofuran, dichloroethane, tetrachloroethane, carbon tetrachloride, trichloroethylene, hexane, heptane, methanol, ethanol, isopropanol or toluene.

Thermoplastic silicone copolymers which can be made into a dispersion or into aqueous emulsions by the usual dispersing or emulsifying techniques can also be employed. To do this, a suitable surface-active agent or dispersing agent must sometimes be added.

The organic segments, blocks or grafts of the thermoplastic silicone copolymers may be, in particular:

polyurethanes (see, for example, Canadian Patent CA-A-1,072,241 and U.S. Pat. Nos. 4,145,508, 4,180,515 and 4,518,758, polyarylenes (see, for example, U.S. Pat. No. 233,427 and FR-A-2,407,950, polystyrenes (see, for example, U.S. Pat. No. 4,263,401), nondegradable polyesters (see, for example, U.S. Pat. No. 3,701,815), polyethers, polycarbonates (see, for example, J. Polym. Sci., Polymer Letters ed. 7,p.569–577) (1969), polyamides, polyimides, polyimides/amides, and generally the thermoplastic silicone copolymers described on pages 181 to 198 of the 1988 edition of Inorganic and Organometallic Polymers.

These organic segments, blocks or grafts are preferably present in a weight content of 5 to 60%, preferably of 8 to 45% by weight, relative to the total weight of the thermoplastic copolymer.

The copolymer is employed as such or in an encapsulating composition where the polymer is mixed with other products which improve the coating (fillers, UV stabilizers, colorants, etc. . . . ) or with the usual additives for the intended application.

The active substance to be encapsulated may be the pure product or a combination of the substance with a suitable carrier, intended to endow it with, inter alia, suitable mechanical properties for use in the process of the invention.

The active substance which can be encapsulated by the process of the invention can therefore be of any kind, as long as its mean particle size is between 50 $\mu$m and 5 mm, and more particularly between 200 $\mu$m and 4 mm.

This active substance may be methionine, an aqueous gel of calcium alginate and, generally more a catalyst, a colorant, a hardener, a detergent, a cosmetic product, a pharmaceutical product, a medication, a vitamin, a perfume, an enzyme, a foodstuff, a metal, an odorant, a plant-protection product, a pesticide, a fungicide, an insecticide, a herbicide, a pheromone, a solid substrate containing an absorbed active constituent, a plant seed, a plant embryo, a meristematic tissue, etc.

Suitable medicaments include:

antiinflammatory agents such as:
  ketoprofen,
  ibuprofen,
  indomethacin,
hormonal agents such as:
  steroids,
  peptide hormones,
antitumoral agents,
antibacterials such as:
  penicillins,
  cephalosporins,
  streptomycins.

The spraying/drying process employed in the process of the present invention is of the type described above; it may be, for example, the Wurster process described in particular in the patents referred to above and in the work by Agis F. Kydonieus, "Controlled Release Technologies", Vol. II (1980), p.133.

According to this process, the particles to be coated (encapsulated) are stirred (fluidized) in a reactor by means of a vertical air stream. A part of the fluidized bed may be determined by a cylindrical part open at both its ends and carrying a vertical air stream at a high velocity, creating a circulation of the particles.

The copolymer, in solution in an organic solvent or in aqueous emulsion or dispersion, is introduced by spraying under pressure inside the fluidized bed of particles and is deposited onto the particles to be coated, while the solvent and/or water is evaporated by the air stream.

In other processes which can be employed within the scope of the present invention, the stirring of the particles is performed mechanically, for example by means of a rotary drum or tray and the gas stream is used only for drying.

To obtain efficient encapsulation it is recommended that the coating film should have an average thickness of between 1 and 200 $\mu$m, preferably between 5 and 100 $\mu$m.

A person skilled in the art using routine tests can obviously easily adapt the thickness of the coating to the nature of the active substance, to its surface quality, to the nature of the copolymer employed, to the desired kinetics of release of the active substance, and the like.

The particles can also be encapsulated, for example, by a first capsule of thermoplastic polymer, and a second layer of a different kind, for example of a natural or synthetic wax, can then be by a different process.

The active substances encapsulated by the thermoplastic organosiloxane block polymers also form part of the invention. They exhibit very advantageous release kinetics when they are administered to man.

Most medications have an "in vivo" activity profile and, for this profile to be attained, require a specific pharmaceutical formulation, particularly when a carefully controlled plasmatic concentration is sought. The availability of the medication over long periods and the ease of the ambulant treatment also introduce requirements in respect of the nature of the formulation excipients. Every patient prefers to take his medicine once daily rather than several times over the same period. In addition, the release of the active substance must take place as uniformly as possible, so as to protect the patient against the painful crises during the latent periods when the active substance is not active, especially in the case of analgesics. The encapsulated active substances of the invention attain this objective.

EXAMPLES

The present invention is described more completely in the following Examples.

EXAMPLE 1

Example 1.a. : Coating of methionine particles

A thermoplastic multiblock copolymer prepared by following the operating procedure described in Example 1 of patent U.S. Pat. No. 4,233,427 is employed in this example.

The α, ω-dihydropolydimethysiloxane employed has an average molecular mass: Mn=8,000 g/mole determined by estimation of the terminal SiH groups.

This copolymer is made up of an alternation of polydimethylsiloxane blocks and of poly[(dimethylsilylene)-phenylene-1,2(dimethylsilylene)ethanediyl] blocks corresponding to the average general formula:

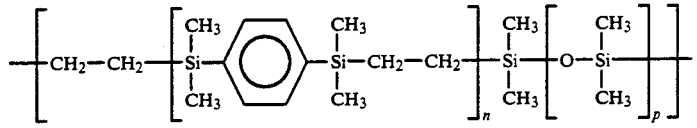

The physicochemical characteristics of the polymers are as follows:
intrinsic viscosity: (20° C., CHCl$_3$): 0.77 dl/g
Mn (number-average molecular mass): 157,000 g/mole
Mw (weight-average molecular mass): 305,000 g/mole
The copolymer contains 75% by weight of polydimethylsiloxane blocks.

The molecular mass is determined by G.P.C. (gel permeation chromatography) at 20° C. in tetrahydrofuran, universal calibration being employed.

This copolymer behaves like an elastomer within a temperature range from approximately −120° C., corresponding to the glass transition temperature of the polydimethylsiloxane part, to 170°/180° C, corresponding to the melting temperature of the semi-crystalline rigid phase.

A Uni-Glatt ® coating apparatus fitted with a Wurster spraying system is employed.

Copolymer (40 g) is dissolved in Prolabo Recta Pur ® 1,2-dichloroethane (725 cm$^3$) at a temperature of approximately 55° C.

Methionine granules (350 g) which have an amino acid content of 98% and a mean particle diameter between 0.8 and 1 mm are charged into the apparatus.

These granules are suspended in a stream of fluidizing air of 70 m$^3$/h at 30° C. (temperature measured at the outlet of the apparatus). The copolymer solution whose temperature is maintained at 40° C. is sprayed within the fluidized bed.

The spraying conditions are as follows:

| | |
|---|---|
| flow rate of copolymer solution | 5 cm$^3$/min, |
| spraying air pressure | 1.5 bar, |
| spraying air temperature | 3° C., |
| spraying time | 2 hours 40 minutes. |

At the end of spraying, methionine particles (376 g) are obtained, that is a weight yield of 96.4%. The coated particles have a methionine weight content of 89%.

The coating ratio obtained, which is the ratio of the weight of the copolymer to the weight of coated methionine is 9%, which corresponds to a copolymer film mean thickness of approximately 15 μm, the thickness being calculated for a copolymer density of 1.

Example 1.b.: release of methionine in aqueous medium from the coated methionine particles The following are charged into a 2-liter glass reactor fitted with a stirrer rotating at 300 revolutions/minute and thermostated at 40° C.:

demineralized water (1 liter),
coated methionine granules (8 grams) prepared in Example 1.a. above,
NaN$_3$ (0.2 g) (bactericide)

The methionine release is evaluated by determining it in samples taken from the aqueous phase at intervals of time. The results obtained are collated in Table I below, where T represents the percentage of methionine released and t the residence time (in hours) of the granules in the aqueous phase.

TABLE I

| t (hours) | 2 | 72 | 144 | 240 | 312 | 360 | 408 | 648 |
|---|---|---|---|---|---|---|---|---|
| T (%) | 3 | 12 | 30 | 50 | 60 | 65 | 70 | 100 |

The release test shows that:
the quantity of methionine released at a time t of less than 30 minutes is practically nil, which shows that the coating is of good quality and that the copolymer does cover the entire surface of the granules,
the methionine is released with release kinetics of an order close to zero and this is generally required in practice in the majority of applications,
microscopic inspection of the particles sampled after 408 hours' immersion in water, shows that the methionine remaining in the granule is in the form of aqueous solution trapped in the spherical copolymer membrane.

EXAMPLE 2

Film-coating of spheres of aqueous gel of calcium alginate

The thermoplastic linear multiblock copolymer employed in this example is defined by the same general formula as the copolymer of Example 1, and is prepared according to the same operating procedure; however, it exhibits different characteristics, which are as follows:
it is prepared from an α,ω-dihydropolydimethylsiloxane with a molecular mass Mn=22,800 g/mole (by determination of end SiH)
its weight content of polydimethylsiloxane is: 90.0%,
its characteristics are as follows: inherent viscosity in chloroform (concentration: 3 g/dl) at 25° C.: 0.39 dl/g.

A solution of this copolymer (10.0 g) in Prolabo Rectapur ® toluene (90 g) is prepared; this is heated to 40° C. and stirred for 10 minutes to make it easier for the copolymer to dissolve.

Spheres of calcium alginate gel (350 g) are then charged into a laboratory Uniglatt ® spraying drying coating apparatus equipped with a spraying system mounted as a "top spray" (spraying via the top of the apparatus, above the fluidized bed).

The alginate spheres are characterized by a mean diameter of 4 mm and a minimum water content of 93% by weight. These spheres are suspended in a stream of fluidizing air of 120 m$^3$/h at 30° C..

The copolymer solution whose temperature is maintained at 40° C., is sprayed into the fluidized bed in the following conditions :

| | |
|---|---|
| flow rate of copolymer solution | 6.7 cm$^3$/min, |
| spraying air pressure | 1.2 bar, |
| spraying air temperature | 30° C., |
| spraying time | 15 minutes. |

At the end of the operation, nonsticky coated spheres (228.6 g) are collected.

This product (100 g) was then taken and was dried in an oven at 60° C. for 24 hours at reduced pressure (13.3 kPa); the drying was finished in the presence of P$_2$O$_5$, until a constant weight was obtained.

The water content of the coated product is: 89.3%.

Surface analysis shows that the alginate spheres are coated with a continuous and hydrophobic film of thermoplastic copolymer.

COMPARATIVE EXAMPLE 3

The operating procedure of Example 2 is repeated exactly, except that a polydimethylsiloxane polymer blocked by a trimethylsilyl group at each end of its chain, with a molecular mass of between 500,000 and 2,000,000 g/mole is employed instead of the thermoplastic copolymer.

The film formed exhibits inadequate mechanical properties and an adhesive nature. In addition, the coated alginate particles agglomerate together during the spraying and in storage.

EXAMPLE 4

Coating of Ketoprofen Granules

1. Synthesis and characteristics of the orgoanosiloxane copolymer employed

An organosiloxane copolymer prepared according to the operating procedure described in Example 4 of patent U.S. Pat. No. 4,233,427 was employed.

The $\alpha,\omega$-dihydropolydimethylsiloxane employed in this preparation has a number-average molecular mass:

$Mn = 22,800$ g/mole (established by determining the SiH functional groups).

This copolymer is made up of an alternation of polydimethylsiloxane segments and of poly(dimethylsilylene)phenylene(dimethylsilylene)-1,2-ethanediyl) segments corresponding to the following general formula:

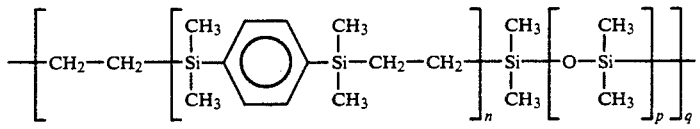

with $\bar{n} \sim 11$ and $p \sim 300$

The proportion of polydimethylsiloxane segments in the copolymer is 90% (by weight).

The inherent viscosity of this copolymer is 0.39 dl/g (measured at 25° C. on a solution in chloroform which has a concentration of 3 g/dl).

2. Coating conditions

A Uni-Glatt ® fluidized bed coating apparatus equipped with a Wurster spraying system is employed.

A copolymer solution is prepared with:
organosiloxane copolymer (55.0 g),
1,2-dichloroethane (997 cc).

Two film-coating operations (A and B) are carried out by following the operating procedure described below. Each test was carried out with ketoprofen granules (350 g) obtained in the following manner: raw materials:

Avicel PH 101, FMC (U.S.),

Courlose, Courtaulds Acetate Ltd (G.B.),

Ketoprofen B. P., Rhone-Poulenc Ltd (G.B.).

The granules were prepared according to an extrusion-spheronization process. Ketoprofen (3 kg) was mixed with Avicel PH 101 (965.6 g) in a Hobart planetary mixer at speed 1. This powder mixture was granulated with a 1.5% (w/w) Courlose solution (2363 g) for 2 minutes. The wet mass was extruded in a Fuji Paudal AXDCS-700 apparatus, marketed by Russel Finex. This apparatus was equipped with a grid pierced with holes 1 mm in diameter and 1 mm in thickness. The cylindrical extruded bodies were then introduced into a machine for rolling spherical granules (JB Caleva Spheronizer) for 3 min and at a speed of 500 rev/min. They were then screened in an apparatus of the Fritsch Sieve Analyser type so as to make their size between 800 and 1400 $\mu$m.

The following film-coating conditions are employed: the temperature of the copolymer solution is maintained in the region of 60° C. throughout the spraying period,

| | |
|---|---|
| Flow rate of the copolymer solution | 6 ml/min, |
| spraying air pressure | 1.5 bar, |
| spraying air temperature | 40° C., | the granules are stirred by a fluidization air flow of 75 m$^3$/h, at a temperature of 30° C.

The other characteristics of these tests are given in the following table:

| TEST No. | VOLUME OF SPRAYED SOLUTION (ML) | CALCULATED COATING CONTENT (%) (1) | KETOPROFEN CONTENT (%) (2) |
|---|---|---|---|
| A | 160 | 2.3 | 65 |
| B | 530 | 7.3 | 62 |

(1) in g of copolymer per 100 g of coated granules
(2) by weight

KINETICS OF RELEASE OF KETOPROFEN IN BUFFERED MEDIUM (pH=6.6) AT 37° C.

Description of the test:

Granules (6 g) and solution at pH = 6.6 (1 liter) are charged into a 1-liter glass reactor fitted with a stirrer and heated by a water bath thermostated at 37° C.

The buffer solution employed was prepared as follows:

dissolving potassium dihydrogen phosphate (KH$_2$PO$_4$) (68 g) in demineralized water (10 liters), adjusting the pH to 6.6 by running in a N sodium hydroxide solution.

The kinetic curves were plotted using ketoprofen determinations carried out at 260 nm on samples of the liquid phase, with a Philips UV/visible spectrophotometer of Pye Unicam PU 8600 type.

The rate of stirring of the granule suspension was 300 rev/min.

The results of these tests are shown in Table II.

TABLE II

| | % OF KETOPROFEN RELEASED AT pH = 6.6, 37° C. | | |
|---|---|---|---|
| TIME (h) | UNCOATED | A | B |
| 0.5 | 42.1 | | |
| 1 | 55.4 | 34.0 | 4.8 |
| 2 | 70.5 | 54.7 | 9.8 |
| 3 | 79.6 | | 19.3 |
| 4 | 85.2 | 77.8 | |
| 5 | | | 23.1 |
| 6 | | | 27.4 |
| 6.5 | 94.0 | | |
| 7 | 96.0 | | 31.1 |
| 8 | | 92.7 | 35.0 |
| 16 | | | 60.3 |
| 19.5 | | | 68.7 |
| 24 | | 100 | 81.0 |
| 26 | | | 84.2 |
| 28 | | | 87.3 |
| 32 | | | 92.6 |
| 48 | | | 100 |

EXAMPLE 5

A thermoplastic multiblock linear copolymer prepared according to the procedure described in Example 1 of patent U.S. Pat. No. 4,233,427 is employed in this example.

The α,ω-dihydropolydimethylsiloxane employed for the synthesis of this copolymer has a number-average molecular mass, Mn, equal to 8600 g/mole (established by determining the end SiH groups).

This copolymer corresponds to the following general formula:

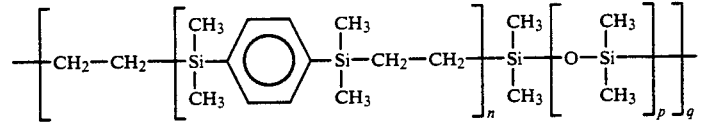

with $\bar{n} \sim 13$ and $p \sim 115$

The proportion of polydimethylsiloxane in this copolymer is 75% by weight.

The inherent viscosity of this copolymer is 0.6 dl/g (measured at 25° C. on a solution in chloroform at a concentration of 3 g of copolymer per dl).

Film-coating

Coating of maize seeds is carried out by spray-coating in an Aeromatic apparatus of Aerocoater Strea-1 type operating with a Wurster system.

A solution of copolymer (7.5 g) in toluene (100 cc) is prepared in a glass receptacle. After Montane 85 (sorbitan trioleate, from Sepic) (2.25 g) has been added as emulsifying agent, an aqueous dispersion (15 cc) containing 500 g/l of Thiodicarb, an insecticidal product of Rhône-Poulenc Agrochimie, is mixed with the solution.

The addition of the aqueous dispersion is carried out at ambient temperature with stirring with a Polytron apparatus rotating at 12,000 revolutions/min, for 2 to 3 minutes.

This mixture obtained in this manner is sprayed with the aid of the Aeromatic apparatus which has been charged beforehand with maize seed (1.5 kg).

The spraying conditions are as follows:

| | |
|---|---|
| flow rate of fluidization air | 140 m³/h |
| fluidization air temperature (exit) | 30–34° C. |
| spraying air pressure | 4 bars |
| spraying time | 17 minutes. |

Determination of Thiodicarb shows that 81.8% of the sprayed insecticidal active substance is found again at the surface of the maize seeds when the operation is complete.

A 9-day germination test, on sand, at 20°-25° C., a batch of untreated bare maize being taken as a control sample, shows that the treatment is not prejudicial to the germination of the seed (90% of germination in the case of the bare control, 96% in the case of the film-coated product).

When compared with a maize treated with Thiodicarb in a traditional manner, without copolymer, the sample treated in this example exhibits a better attrition resistance, and a better persistence of the insecticide around the seed (by virtue of the controlled release effect contributed by the copolymer).

These advantages have been demonstrated by the following tests:

Attrition resistance

Seed (50 g) is placed in a glass receptacle which is agitated for 10 minutes with the aid of a Turbula trademark apparatus rotating at 48 revolutions/minute. The quantity of the fines formed during the operation is weighed.

Water elution resistance

Seed (20 g) is placed in a column into which water (1 liter) is run at a rate of 12 ml/min. At the end of the test, the percentage of active substance in the sample is determined.

| | Result of the tests: | |
|---|---|---|
| Sample | ATTRITION fines per 100 g of maize | ELUTION Residual THIODICARB, as % of the initial content |
| Thiodicarb treated maize control (traditional treatment) | 0.417 | 57.3 |
| Sample of the example, Thiodicarb/ copolymer treated | 0.085 | 98.5 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference .

We claim:

1. A process for encapsulating particles of an active substance having a particle size of between 50 μm and 5 mm, which comprises film-coating each particle with a thermoplastic linear silicone polymer, by spraying onto each particle said thermoplastic linear silicone copolymer in a solution of an organic solvent or in an aqueous emulsion or disperson, and evaporating said solvent and/or water to form an encapsulated particle having a zero order of release, said thermoplastic linear silicone copolymer softens when heated, is soluble in volatile organic solvents and/or emulsifiable or dispersible in water and is a linear multiblock copolymer, a block copolymer or a graft copolymer, whose substantially linear main polymer chain consists either of an alternation of polydiorganosiloxane segments or blocks and of organic segments or blocks, or of a polydiorganosiloxane chain onto which organic chains are grafted.

2. Process according to claim 1, wherein the segments, blocks or grafts of the thermoplastic linear silicone copolymer are selected from the group consisting of polyurethanes, polyarylenes, polystyrenes, polyesters, polyethers, polycarbonates, polyamides, polyimides and polyimides/amides.

3. Process according to claim 2, wherein the weight content of the organic segments, blocks or grafts is between 5 and 60%.

4. Process according to claim 1, wherein the thermoplastic silicone copolymer has a glass transition temperature or a melting temperature above 40° C.

5. Process according to claim 1, wherein the said active substance is an alimentary, plant-protection or medicinal active substance.

6. Process according to claim 5, wherein the said active substance is an antiinflammatory agent, hormone, antibacterial or antitumoral agent.

7. Process according to claim 1, wherein the said active substance is a plant seed or embryo.

* * * * *